United States Patent
Jager-Lezer

(10) Patent No.: US 7,754,196 B2
(45) Date of Patent: Jul. 13, 2010

(54) COSMETIC COMPOSITION COMPRISING FIBER

(75) Inventor: Nathalie Jager-Lezer, Verrieres-le-Buisson (FR)

(73) Assignee: L'Oreal, Paris (FR)

( * ) Notice: Subject to any disclaimer, the term of this patent is extended or adjusted under 35 U.S.C. 154(b) by 1145 days.

(21) Appl. No.: 10/664,894

(22) Filed: Sep. 22, 2003

(65) Prior Publication Data

US 2004/0096473 A1 May 20, 2004

Related U.S. Application Data

(60) Provisional application No. 60/416,240, filed on Oct. 7, 2002.

(30) Foreign Application Priority Data

Sep. 20, 2002 (FR) .................................. 02 11673

(51) Int. Cl.
*A61Q 1/10* (2006.01)
*A61Q 1/00* (2006.01)
(52) U.S. Cl. ..................................... 424/70.7; 424/401
(58) Field of Classification Search ........................ None
See application file for complete search history.

(56) References Cited

U.S. PATENT DOCUMENTS

| | | | |
|---|---|---|---|
| 3,802,841 A | 4/1974 | Jean-Baptiste | |
| 5,324,506 A | 6/1994 | Calvo et al. | |
| 5,911,974 A * | 6/1999 | Brieva et al. | 424/64 |
| 6,491,931 B1 * | 12/2002 | Collin | 424/401 |
| 6,503,521 B1 | 1/2003 | Atis et al. | |
| 6,726,917 B2 * | 4/2004 | Kanji et al. | 424/401 |
| 6,955,805 B2 | 10/2005 | Shah et al. | |
| 2002/0098217 A1 | 7/2002 | Piot et al. | |
| 2003/0031642 A1 | 2/2003 | Lezer | |
| 2004/0142831 A1 | 7/2004 | Lezer | |
| 2006/0057085 A1 | 3/2006 | Lezer | |

FOREIGN PATENT DOCUMENTS

| | | |
|---|---|---|
| EP | 0 445 342 | 9/1991 |
| EP | 1 053 742 | 11/2000 |
| EP | 1 201 221 | 5/2002 |
| EP | 1 208 836 | 5/2002 |
| JP | 09-263 518 | 10/1997 |
| JP | 2000-344627 | 12/2000 |
| JP | 2001-48736 | 2/2001 |
| JP | 2001-48750 | 2/2001 |
| JP | 2002-145739 | 5/2002 |
| JP | 2002-154932 | 5/2002 |
| JP | 2002-173412 | 6/2002 |
| JP | 2004-155768 | 6/2004 |
| WO | WO 00/72809 | 12/2000 |

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

Cosmetic composition comprising rigid, substantially rectilinear fibers of a synthetic polymer in a physiologically acceptable medium, in which the polymer is chosen from polyurethanes, polyesters, acrylic polymers, polyolefins, non-aromatic polyamides and aromatic polyimide-amides.

The composition may be a makeup composition, a makeup base, a composition to be applied over a makeup, also known as a "top coat", or a cosmetic treatment or care composition for keratin fibres. The invention relates more particularly to a mascara.

The invention also relates to the use of this composition for making up keratin materials, especially the eyelashes, the eyebrows and the hair, and also to a cosmetic makeup or care process for these materials.

33 Claims, No Drawings

COSMETIC COMPOSITION COMPRISING FIBER

REFERENCE TO PRIOR APPLICATIONS

This application claims priority to U.S. provisional application 60/416,240 filed Oct. 7, 2002, and to French patent application 02 11673 filed Sep. 20, 2002, both incorporated herein by reference.

The present invention relates to a cosmetic makeup or care composition for keratin materials, comprising fibres.

The invention also relates to the use of this composition for making up keratin materials, especially the eyelashes, the eyebrows and the hair, and also to a cosmetic process for making up or caring for these materials.

The composition and the makeup process according to the invention are more particularly intended for human keratin fibres, especially substantially longilinear fibres, such as the eyelashes, the eyebrows and the hair, including false eyelashes; the composition and the makeup process according to the invention are preferably intended for the eyelashes.

The composition may be a makeup composition, a makeup base, a composition to be applied over a makeup, also known as a "top coat", or a composition for the cosmetic treatment or care of keratin fibres. The invention more particularly relates to a mascara.

It is known practice, in this technical field, to use fibres in makeup or care compositions for keratin materials to improve their cosmetic properties.

Thus, it is known practice from document JP-A-3 151 613 to use fibres in mascara compositions to give the eyelashes a lengthening and thickening effect. Documents JP-A-57 158 714 and JP-A-9 263 518 describe mascara compositions comprising fibres and polymers of acrylic type in aqueous dispersion.

Similarly, documents JP-A-6 9340 and JP-A-7 179 323 describe mascara compositions comprising fibres and polymers in aqueous dispersion.

Document FR-A-2 817 477 describes cosmetic compositions or formulations comprising fibres based on a synthetic or artificial polymer, such as polypropylene, PET, polyamide 6 and polyamide 66.

However, the cosmetic compositions containing fibres of the prior art have a certain number of drawbacks, such as a heterogeneous and relatively imprecise makeup result.

In particular, the mascara compositions containing fibres of the prior art do not make it possible to obtain an optimum lengthening effect of the eyelashes after application of the composition. The reason for this is that the fibres are oriented and distributed randomly on the eyelashes rather than lying in line with the eyelashes.

The effect obtained by the mascara compositions containing fibres of the prior art is often aesthetically unacceptable, especially in the case of dense and/or long and/or curved eyelashes, for which a particularly unsightly "Christmas tree" appearance of the eyelashes is obtained.

There is thus a need for a cosmetic composition, in particular a mascara composition, which affords excellent cosmetic properties and a homogeneous and precise makeup result.

There is especially a need for a mascara composition that affords perfect lengthening, in the exact continuation of the eyelash, a regular, nonrandom positioning of the fibres exactly in line with the eyelash and thus an optimum aesthetic and lengthening effect.

In addition, this composition should preferably maintain the lengthening effect over time.

The aim of the present invention is, inter alia, to meet the needs and satisfy the requirements mentioned above.

This aim and others are achieved, in accordance with the invention, by a cosmetic composition comprising rigid, substantially rectilinear fibres of a synthetic polymer in a physiologically acceptable medium, in which the polymer is chosen from polyurethanes, polyesters, acrylic polymers, polyolefins, non-aromatic polyamides and aromatic polyimide-amides. Advantageously, at least 50%, preferably at least 75% and better still at least 90%, in numerical terms, of the fibres are such that the angle formed between the tangent to the central longitudinal axis of the fibre at one of the ends of the fibre and the straight line connecting the said end to the point on the central longitudinal axis of the fibre corresponding to half the length of the fibre, is less than or equal to 15°, and the angle formed between the tangent to the central longitudinal axis of the fibre at a point halfway along the fibre and the straight line connecting one of the ends to the point on the central longitudinal axis of the fibre corresponding to half the length of the fibre, is less than or equal to 15°, for the same length of fibre ranging from 0.8 mm to 5 mm, preferably ranging from 1 to 4 mm, more preferably from 1 to 3 mm and better still 2 mm.

Advantageously, the angle mentioned above is measured at both ends of the fibre and at a point halfway along the fibre, in other words three measurements are taken in this case and the mean of the angles measured is less than or equal to 15°.

The tangent, at any point on the fibre, especially forms an angle of less than or equal to 15°.

In the present patent application, the angle formed by the tangent at a point on the fibre is the angle formed between the tangent to the central longitudinal axis of the fibre at the said point on the fibre and the straight line connecting the end of the fibre that is closer to the said point to the point on the central longitudinal axis of the fibre corresponding to half the length of the fibre.

Generally, the fibres included in the composition have the same fibre length or a substantially identical length.

The composition according to the invention differs fundamentally from the compositions of the prior art; firstly, among the innumerable types of fibres that may be incorporated into a cosmetic composition, such as mineral, synthetic and natural fibres, only five specific families of fibres have been selected, which are, according to the invention, synthetic polymer fibres, the said synthetic polymer being chosen from polyurethanes, polyesters, acrylic polymers, polyolefins, non-aromatic polyamides and aromatic polyimide-amides (or polyamide-imides).

A very limited number of types of synthetic polymer that differ in terms of their structure have thus been chosen to be incorporated into the compositions of the invention.

In addition, the fibres in the compositions according to the invention are defined by a particular parameter lying in a particular range. This parameter is, for the same fibre length ranging from 0.8 mm to 5 mm, preferably ranging from 1 to 4 mm, more preferably from 1 to 3 mm and better still 2 mm, the angle formed by (between) the tangent to the central longitudinal axis of the fibre at one of its ends and the straight line connecting the said end to the point on the central longitudinal axis of the fibre corresponding to or located halfway along the length of the fibre, which must, according to the invention, be less than or equal to 15°, preferably less than or equal to 10° and more preferably less than or equal to 5°, and the angle formed between the tangent to the central longitudinal axis of the fibre at a point located halfway along the fibre and the straight line connecting one of the ends to the point on the central longitudinal axis of the fibre corresponding to half the length of the fibre, which must, according to the invention, be less than or equal to 15°, preferably less than or equal to 10° and more preferably less than or equal to 5°. This angle condition must furthermore be satisfied by at least a majority of the fibres, i.e. 50% of the fibres, preferably at least 75% of the fibres and better still at least 90% of the fibres, in numerical terms.

More specifically, according to the invention, when a medium in which the fibres are dispersed at a fibre concentration of 1% by weight is observed under a microscope, using an objective lens allowing a magnification of 2.5 and with full field vision, a majority of the fibres, i.e. at least 50% of the fibres, preferably at least 75% of the fibres and better still at least 90% of the fibres, in numerical terms, must satisfy the angular condition defined above. The measurement leading to the angle value is performed for the same fibre length, this length being in the range from 0.8 mm to 5 mm, preferably from 1 to 4 mm, more preferably from 1 to 3 mm and better still 2 mm. The full field vision allows the fibres to be viewed in their entirety.

The medium in which the observation is performed is a dispersing medium ensuring good dispersion of the fibres, for example water, an aqueous gel of clay or associative polyurethane. A direct observation of the composition containing the fibres may also be performed.

In fact, the fibres included in the compositions of the invention may also be defined as being rigid fibres, as opposed to the fibres in the compositions of the prior art, which are not rigid fibres and consequently form curls with relatively large curvature when observed under a microscope.

In other words, the fibres in the compositions of the invention, which are initially substantially straight, when placed in a dispersing medium, do not undergo a substantial change in shape, which is reflected by the angular condition defined above, representing a shape that can still be described as substantially straight, linear and rectilinear, a "stick" shape.

This angle condition reflects the conserved rigidity of the fibres, which may be expressed with difficulty by a parameter other than the one chosen according to the invention for objects that are as small as the fibres used in the compositions of the invention.

More exactly, the angle condition which the fibres in the compositions of the invention must satisfy illustrates the conservation of the shape of the fibres, which remains substantially rectilinear, on account of the rigidity of the fibre.

With the fibres of the prior art, which are not in the form of "straight sticks" and therefore do not satisfy the angle condition of the fibres in the compositions of the invention, the lengthening effect cannot be obtained and is therefore not optimized.

Fibres of the prior art, which are flexible, do not have a shape that is initially rectilinear, and when they are placed in a dispersing medium such as a cosmetic composition, these fibres become deformed forming curls, give no lengthening effect and make the eyelash look unattractive. To use a trivial comparison, the fibres according to the invention may be compared to spaghetti before cooking, which is rigid and rectilinear, and they retain this shape, whereas the fibres of the prior art, which are flexible, may be compared to cooked spaghetti, that becomes deformed, curls and cannot maintain a rectilinear shape.

The compositions of the invention, incorporating the specific fibres described above, have excellent cosmetic properties; in particular they allow homogeneous and precise makeup, in the case of mascaras. The fibres in the compositions of the invention are not arranged randomly, but become placed in line with the eyelashes. In fact, the composition according to the invention gives the eyelashes a very good lengthening effect, by virtue of the particular fibres it contains, which become placed perfectly, exactly in line with the eyelash. The composition of the invention in fact makes it possible to produce a veritable eyelash "prosthesis", which is entirely impossible with the compositions of the prior art, containing non-rigid fibres.

The mascara compositions according to the invention provide perfect lengthening and an optimum aesthetic effect, even in the case of dense and/or long and/or curled eyelashes, for which particularly unattractive effects were obtained with the compositions of the prior art, comprising non-rigid fibres that curl.

The mascara compositions according to the invention produce a perfect continuity of the eyelash, to the extent that the fibres can no longer be observed with the naked eye because they are exactly in line with the eyelash and "mimic" it perfectly.

The term "fibre" should be understood as meaning an object of length L and diameter D such that L is generally very much greater than D, D being the diameter of the circle within which the cross section of the fibre is inscribed. In particular, the ratio L/D (or shape factor) is chosen in the range from 3.5 to 2 500, preferably from 5 to 500 and better still from 5 to 150.

The fibres that may be used in the composition of the invention may be individual or organized, for example braided, hollow or solid. They may have any shape, i.e. cross-section shape, and the cross section may especially be circular or polygonal, for example triangular, square, hexagonal or flat octagonal or may be multilobal (clover-shaped), depending on the specific application envisaged. Generally, their ends are blunted and/or polished to prevent injury. In addition, the fibres used in the composition of the invention are not fibres, for example flat fibres, with a multilayer polymer structure (comprising at least two layers) such that the multilayer structure creates a colour effect by means of interference of light rays, which diffract and diffuse differently depending on the layers; such fibres are described in documents EP-A-911 217, EP-A-686 858 and U.S. Pat. No. 5,472,798.

Generally, the fibres have a length ranging from 0.8 to 5 mm, preferably from 1 to 4 mm and better still ranging from 1 mm to 3 mm, for example 2 mm. Their cross section may be within a circle having a diameter ranging from 2 nm to 500 µm, preferably ranging from 100 nm to 100 µm and better still from 1 µm to 50 µm.

The weight or yarn count of the fibres is often given in denier and represents the weight in grams per 9 km of yarn. Preferably, the fibres according to the invention have a yarn count chosen in the range from 0.15 to 30 denier and better still from 0.18 to 18 denier.

The fibres may be present in the composition according to the invention in a content ranging from 0.01% to 10% by weight, preferably from 0.1% to 5% by weight and better still from 0.3% to 3% by weight, relative to the total weight of the composition.

The fibres according to the invention are chosen from non-aromatic polyamide fibres, such as certain Nylons®, acrylic polymer fibres, polyolefin fibres and especially polyethylene or polypropylene fibres, polyester fibres, polyurethane fibres and aromatic polyimide-amide fibres, such as the Kermel® and Kermel Tech® fibres from Rhodia, and fibres formed from a blend of polymers, such as those mentioned above, for instance polyamide/polyester fibres.

Examples of rigid fibres that may be mentioned include:
 rigid polyester fibres, such as those obtained by chopping yarns sold under the names Fibre 255-100-R11-242T Size 3 mm (eight-lobed cross section), Fibre 265-34-R11-56T Size 3 mm (round cross section), Fibre Coolmax 50-34-591 Size 3 mm (four-lobed cross section) by the company Dupont de Nemours;

rigid polyamide fibres, such as those sold under the names Trilobal Nylon 0.120-1.8 DPF; Trilobal Nylon 0.120-18 DPF; Nylon 0.120-6 DPF by the company Cellusuede Products; or obtained by chopping yarns sold under the name Fibre Nomex Brand 430 Size 3 mm by the company Dupont de Nemours.

Moreover, the fibres may or may not be surface-treated and may or may not be coated, for example with an active agent and/or a dye and/or a pigment.

The coating or deposition, for example of active agent and/or pigment and/or dye, onto the fibres may be performed by dipping the fibres in a solution of active agent, in order to graft or adsorb the active agent onto the surface of the fibres.

An active agent and/or pigment and/or dye may also be incorporated in the very bulk of the polymer in the matrix of the polymer forming the fibres. The presence of the active agent within the fibre makes it possible to improve its stability, especially if it is an active agent that is sensitive to degradations of any kind.

By incorporating the active agent into or onto the fibres, greater diffusion of the active agent is obtained over a longer period, since the fibres remain at the surface of the skin and allow optimum diffusion of the active agent, whereas, when this active agent is used in isolation, without being incorporated into a fibre, it is attacked and removed by the bodily fluids, such as sebum, tears, etc.

In other words, the inclusion of the active agent and/or pigment and/or dye into the fibre results in an effect that may generally be described as a remanence effect.

The products Kermel® and Kermel Tech®, for example, are dyed in the bulk, which affords very long durability of the colours over time.

Advantageously, water-insoluble fibres may be used.

However, the fibres that are particularly preferred, which may be incorporated into the compositions of the invention, are aromatic polyimide-amide or polyamide-imide fibres, such as the Kermel® and Kermel Tech® fibres from Rhodia.

The incorporation of these very specific aromatic polyimide-amide fibres into cosmetic compositions, such as mascara compositions makes it possible to obtain all the beneficial effects mentioned above, in particular as regards the lengthened and eyelash "mimic" effects.

Obviously, these polyamide-imide fibres satisfy the condition of rigidity and curling, which all the fibres used according to the invention must satisfy.

These fibres show good cosmetic harmlessness; good chemical resistance to solvents and good mechanical strength.

The aromatic polyimide-amides included in the composition of the fibres according to the invention may be any aromatic polyimide-amides, but generally comprise a repeating unit corresponding to the general formula (I) below:

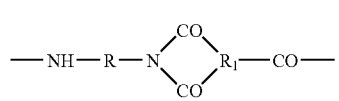

(I)

These aromatic polyimide-amides also optionally comprise a repeating unit ("amide" unit) of formula (II):

—NH—R—NH—CO—R$_2$—CO—  (II)

These aromatic polyimide-amides also optionally comprise a repeating unit ("amide" unit) of formula (III):

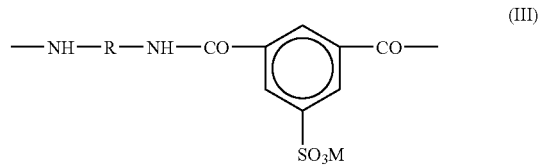

(III)

These aromatic polyimide-amides also optionally comprise a repeating unit ("amide" unit) of formula (IV):

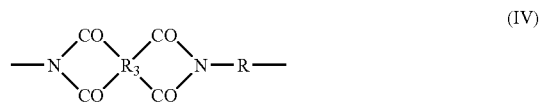

(IV)

in which R represents a divalent aromatic group, $R_2$ represents a divalent aromatic group, $R_3$ represents a tetravalent aromatic group, $R_1$ represents a trivalent aromatic group and M represents an alkali metal or alkaline-earth metal.

For example, R and $R_2$ each independently represent a divalent group comprising at least one optionally substituted aromatic ring containing from 6 to 10 carbon atoms and/or an optionally substituted heterocycle of aromatic nature containing from 5 to 10 atoms and comprising one or more hetero atoms chosen from S, N and O;

$R_1$ represents a trivalent group comprising at least one optionally substituted carbon-based aromatic ring containing from 6 to 10 carbon atoms and/or an optionally substituted heterocycle of aromatic nature containing from 5 to 10 carbon atoms and comprising one or more hetero atoms chosen from S, N and O.

In formula (I) mentioned above, $R_1$ may be, for example, a benzene ring optionally substituted with one or two substituent(s) chosen from alkyl and alkoxy groups of 1 to 10 C, halogen atoms, a nitro group and a sulphonyl group; or several benzene rings optionally substituted with one or more substituents chosen from alkyl and alkoxy groups of 1 to 10 C, halogen atoms, a nitro group and a sulphonyl group; for example, $R_1$ may comprise from 2 to 5 rings, linked together via a single bond or via a divalent group, the chain of the said rings possibly being independently in the meta or para position.

The said divalent group linking the said rings is chosen, for example, from:

a divalent group derived from a linear or branched alkyl group (for example an alkylidene or alkylene group) of 1 to 10 C, optionally substituted, preferably on the same carbon, with one or more halogens chosen from F, Cl, Br and I and/or with one or more hydroxyl groups, the said divalent group more preferably being a divalent group derived from a perfluoroalkyl group, for example perfluoroalkylene;

a hetero atom chosen from O and S;

a group

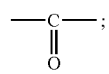

a group

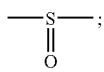

a group

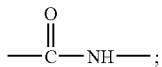

a group

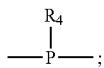

a group

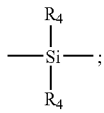

a group

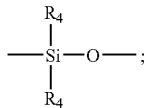

in which $R_4$ is chosen from alkyl groups of 1 to 10 C such as methyl, ethyl, isopropyl, etc.

$R_1$ may also represent a fused polycyclic carbon-based group optionally substituted with one or more substituents chosen from alkyl groups and alkoxy groups of 1 to 10 C, halogen atoms, a nitro group and a sulphonyl group, the said polycyclic carbon-based group comprising, for example, from 2 to 5 benzene rings chosen, for example, from naphthalene, phenanthrene, coronene, perylene, phenylindane, etc.

$R_1$ may also represent a heterocycle or a fused heterocycle of aromatic nature, such as thiophene, pyrazine, pyridine, furan, quinoline, quinoxaline or isobenzofuran, this heterocycle optionally being substituted with one or more substituents chosen from alkyl (for example methyl, ethyl, isopropyl, etc.) and alkoxy groups of 1 to 10 C, halogen atoms (F, Cl, Br or I), a nitro group and a sulphonyl group.

Among the polyimide-amides that may be used in the context of the invention, mention will be made of those in which $R_1$ is a benzene ring, a combination of two benzene rings linked together via an oxygen bridge, or a naphthalene ring.

The preferred groups $R_1$ are:

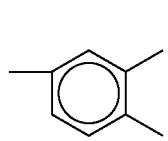

and

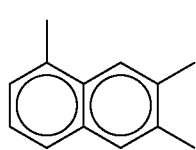

The group $R_3$ corresponds to the same definition as the group $R_1$, except that it is a tetra-valent group rather than a trivalent group.

R and $R_2$, which may be identical or different, each represent, for example, a divalent benzene ring with chains in the meta or para position; optionally substituted with one or more substituents chosen from alkyl and alkoxy groups of 1 to 10 C such as methyl, ethyl, isopropyl, butyl, methoxy, etc., halogen atoms, a nitro group and a sulphonyl group; or several benzene rings optionally substituted with one or more substituents chosen from alkyl and alkoxy groups of 1 to 10 C, halogen atoms, a nitro group and a sulphonyl group; for example, R and $R_2$ may comprise from 2 to 5 rings linked together via a simple bond or via a divalent group.

The said divalent group linking the benzene rings of R or $R_2$ is chosen, for example, from:
  a divalent group derived from a linear or branched alkyl group (for example an alkylidene or alkylene group) of 1 to 10 C, optionally substituted, preferably on the same carbon atom, with one or more halogens chosen from F, Cl, Br and I and/or with one or more hydroxyl groups; the said divalent group is more preferably a divalent group derived from a perfluoroalkyl group, for example perfluoroalkylene;
  a hetero atom chosen from O and S;
  a group

a group

a group

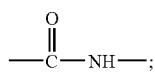

a group

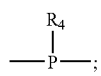

a group

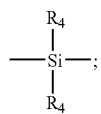

a group

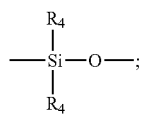

in which $R_4$ is chosen from alkyl groups of 1 to 10 C such as methyl, ethyl, isopropyl, etc.

R and $R_2$ may also each represent a divalent fused polycyclic carbon-based group optionally substituted with one or more substituents chosen from alkyl and alkoxy groups of 1 to 10 C, halogen atoms, a nitro group and a sulphonyl group; the said polycyclic carbon-based group may comprise, for example, from 2 to 5 benzene rings and may be chosen, for example, from naphthalene, phenanthrene, coronene, perylene, phenylindane, etc.

$R_2$ may also represent a heterocycle or a fused heterocycle of aromatic nature, for example thiophene, pyrazine, pyridine, furan, quinoline, quinoxaline or isobenzofuran, this heterocycle optionally being substituted with one or more substituents chosen from alkyl and alkoxy groups of 1 to 10 C, for example methyl, ethyl, isopropyl or methoxy, halogen atoms (F, Cl, Br or I), a nitro group and a sulphonyl group.

The preferred polyimide-amides are those in which R is a diphenylmethane group and $R_2$ is a phenyl-1,4-diyl group; or R is a diphenyl ether group and $R_2$ is a phenyl-1,4-diyl group.

Examples of the group $R_1$ have already been given above:

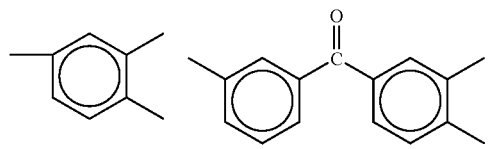

and

Examples of the group $R_3$ are the following:

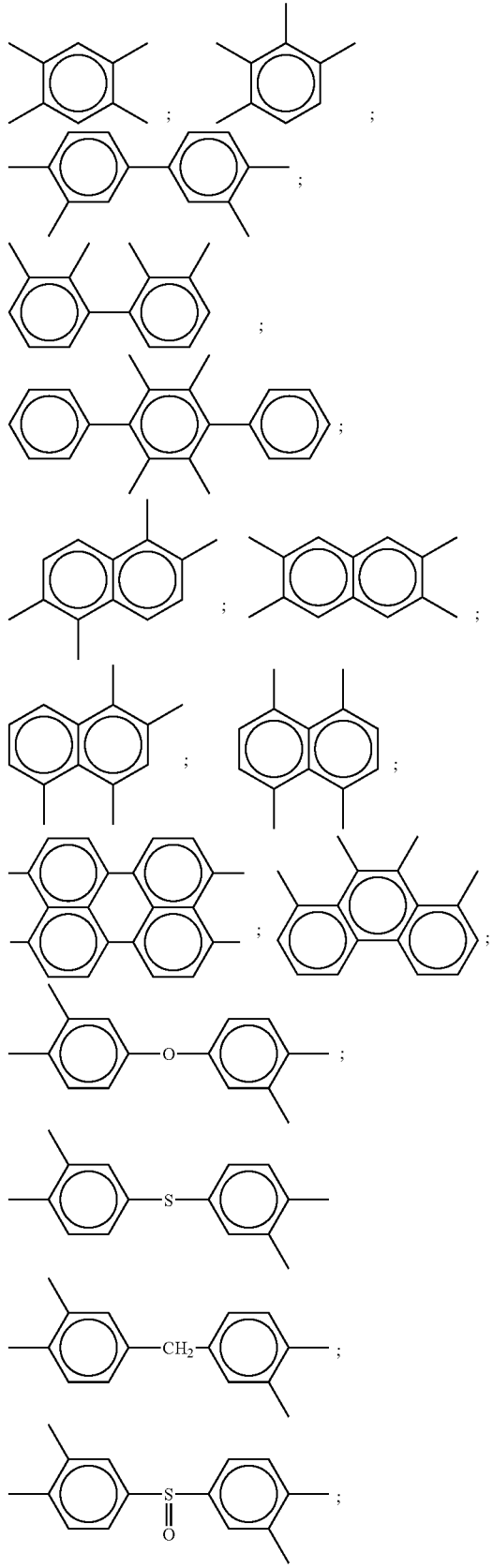

-continued
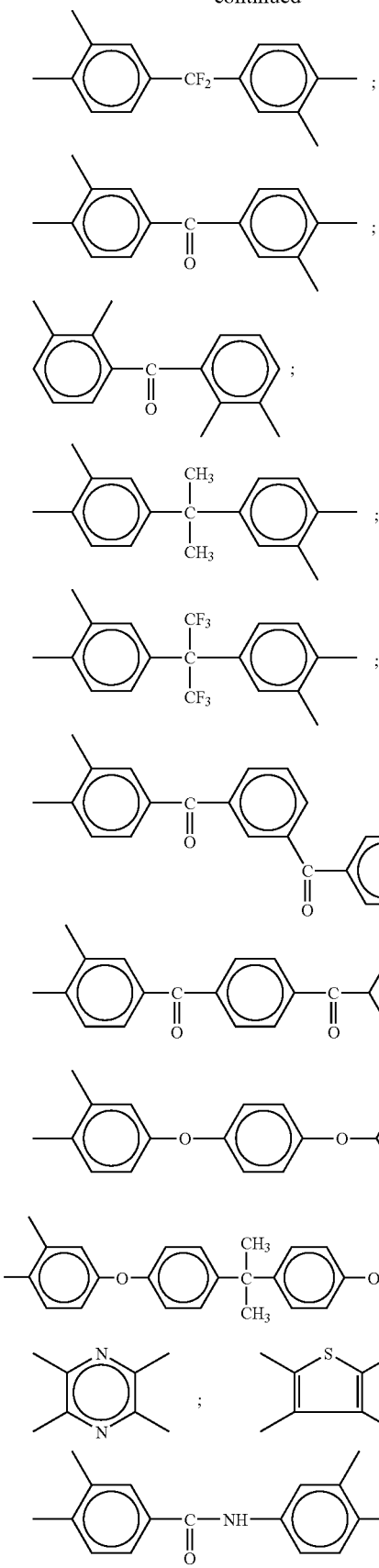
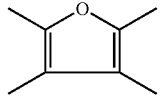
It should be noted that other examples of groups $R_1$ are the trivalent equivalents of the tetravalent groups $R_3$ illustrated above.
Examples of the groups R and $R_2$ are the following:
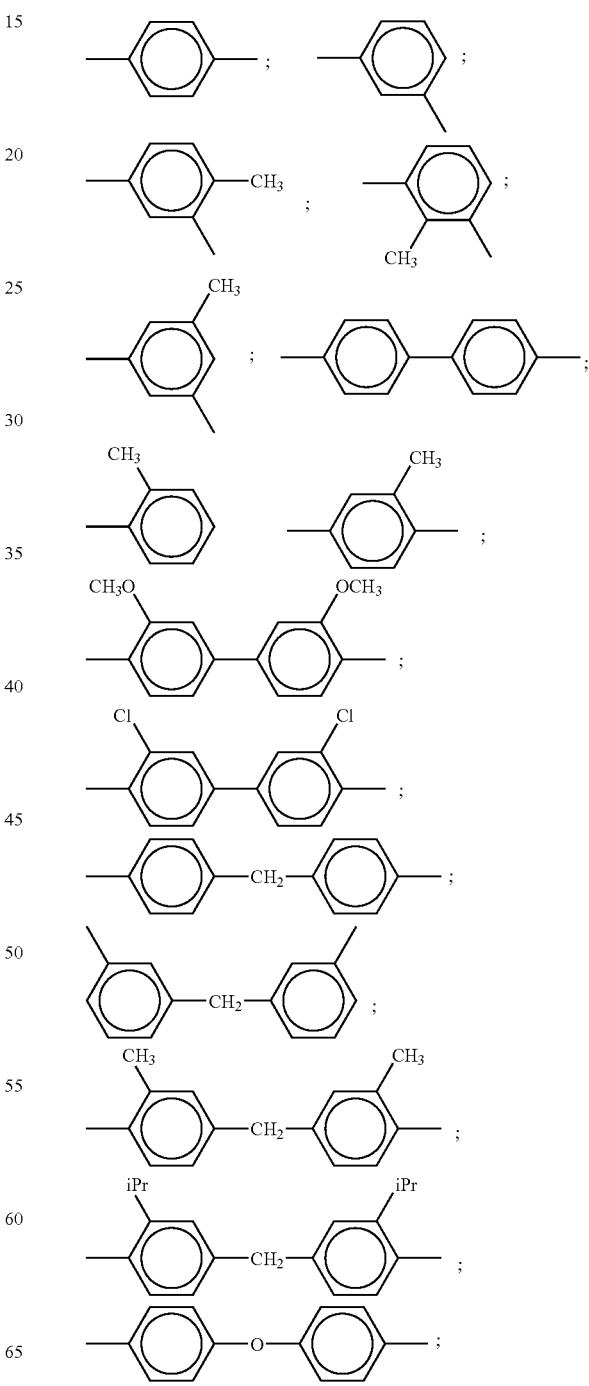

-continued

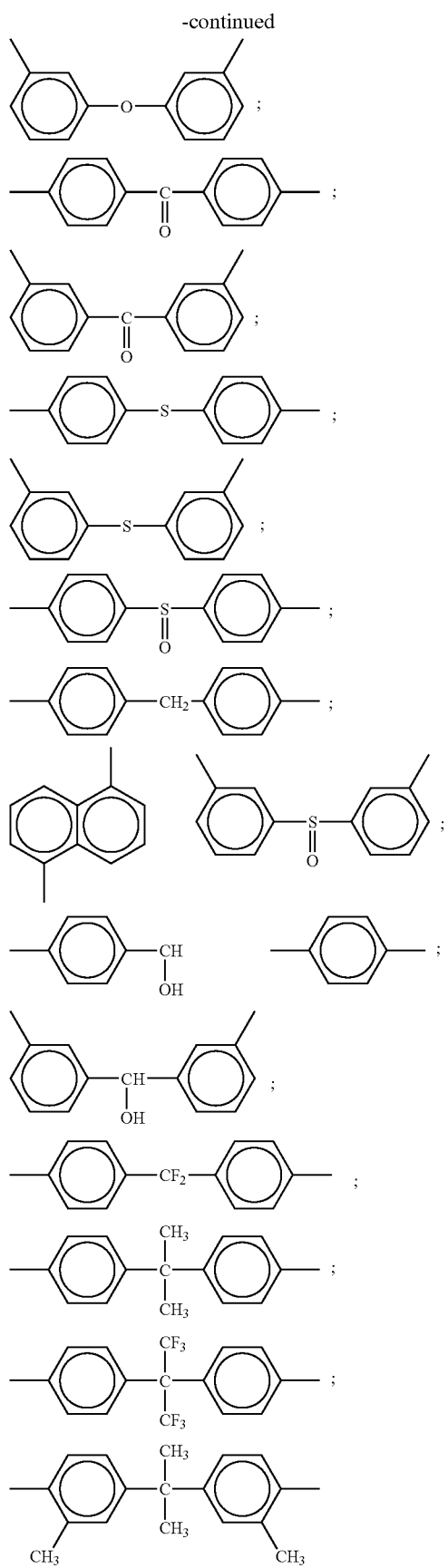

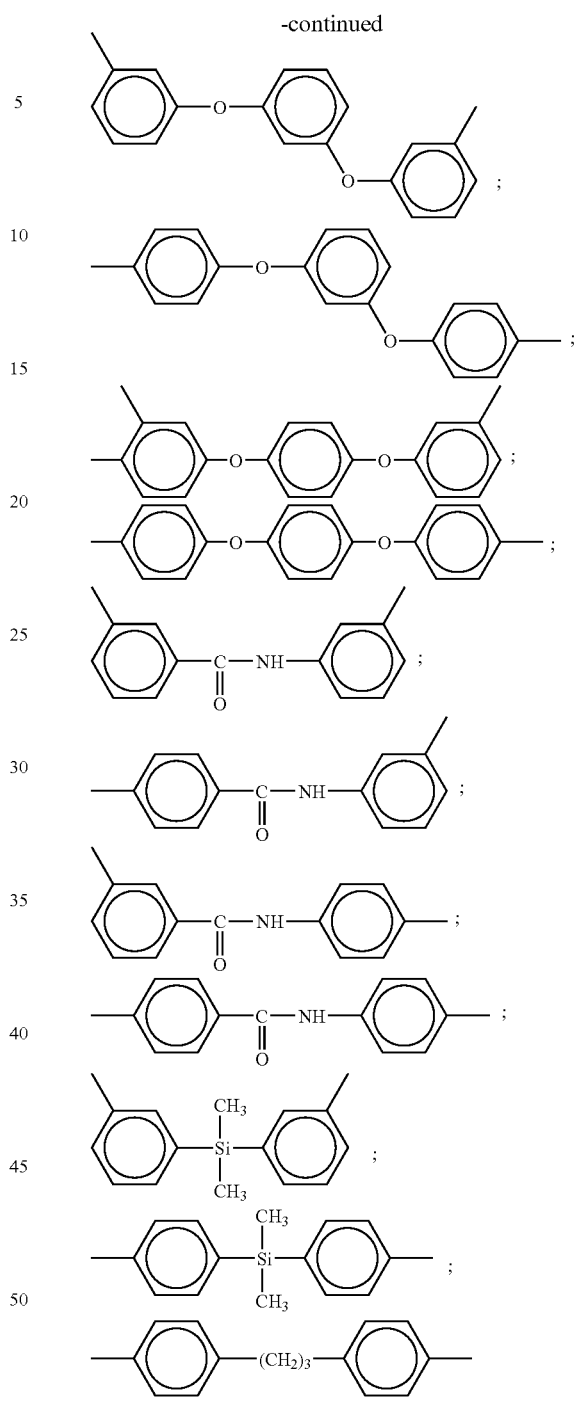

The aromatic polyimide-amides forming the fibres used in the composition of the invention may be obtained by any process known to those skilled in the art for preparing aromatic polyimide-amides, preferably by reacting a diisocyanate with trimellitic anhydride.

Preparation processes are described especially in the documents by Pigeon and document U.S. Pat. No. 3,802,841, cited below.

Polyimide-amide yarns or fibres that may be used for the compositions of the invention are described, for example, in the document by R. Pigeon and P. Allard, Chimie Macromoléculaire Appliquée, 40/41 (1974), pages 139-158 (No. 600), to which reference may be made. The polyamide-imide is prepared by direct polycondensation of trimellitic anhydride with an aromatic diisocyanate of formula:

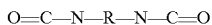

with removal of the $CO_2$.

The aromatic diisocyanate may be replaced with its urethane derivative of formula:

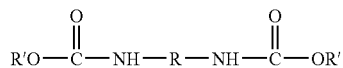

In these formulae, R, which may have the meaning already given above, preferably represents:

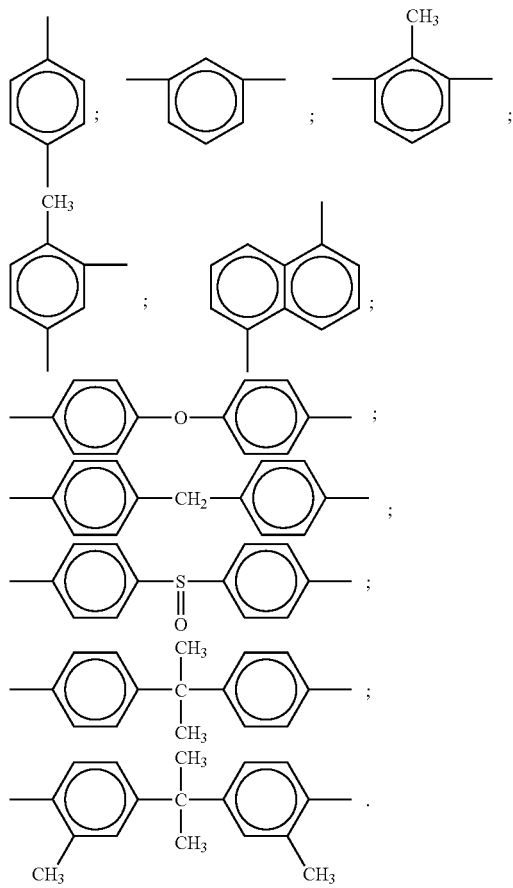

In addition, a copolyimide-imide may also be obtained by partially replacing the trimellitic anhydride (TMA) with a dicarboxylic acid or a dianhydride (third component), which results in a modification of the a mide/amide ratio in the polymer. The third component may be chosen from isophthalic acid, terephthalic acid, diphenylic acid, phenylindanedicarboxylic acid and pyromellitic anhydride. This third component may be present in a proportion that may range up to 10, 20, 30 or 40 mol % relative to the mixture of TMA and third component.

The reaction of trimellitic anhydride with a diisocyanate is performed in a polar solvent, such as DMF, DMAC or NMP, and mixtures thereof. The solvents and reagents are preferably of high purity.

The reagents, in stoichiometric amount, are added with stirring to a reactor, heated according to a given heating programme, and the reaction is stopped by cooling, when the correct viscosity is obtained.

For example, the reaction, especially to obtain polydiphenylmethane trimellitide amides, may be performed by heating at from 80 to 150° C., for 3.5 hours, followed by heating at 450° C. for 4.5 hours, or by heating for 8 hours at from 80° C. to 150° C., for example from 80, 120 or 150° C.

After adjusting the concentration and filtering, the solution is spun according to the known wet-route and dry-route processes and the yarns are chopped to the desired fibre length to be incorporated into the compositions according to the invention.

The spinning takes place, without any particular difficulties, either via a dry-route process or via a wet-route process, provided that there is a correct ratio between the viscosity and the concentration.

In the dry-spinning operation, the solution is compressed using a titration pump by means of a spinning nozzle that is at the top end of a vertically heated tank. The solvent evaporates under the action of the flow of gas and is trapped again by condensation.

In the wet-spinning operation, the spinning nozzle is immersed in a precipitated bath of water and solvent. In this bath, the polymer is precipitated in the form of a gel of monofilaments which are then partially drawn, washed and dried. It should be pointed out, however, that to completely remove the solvent, a washing treatment that is more thorough than for traditional fibres spun using a solution must be performed. Other additives may be added to the spinning solution without any problems, especially pigments. In this way, a series of colours showing good fastness, both for endless yarns and fibre yarns, may be obtained.

Other polyimide-amides that may be used to form the fibres in the compositions of the invention are described in document U.S. Pat. No. 3,802,841, to the description of which reference may also be made.

This US document describes the preparation of polyimide-amides by reacting a diamine or a derivative thereof, such as an aromatic diisocyanate, with an acid anhydride or a derivative thereof.

The aromatic diisocyanates are, for example, tolylene diisocyanate, 4',4'-diisocyanatodiphenyl-methane, 4',4'-diisocyanatodiphenylpropane and 4'-diisocyanatodiphenyl ether. Thus, in this document, a polycarboxylic acid, preferably a tricarboxylic acid, is reacted with one or more diamines. The polycarboxylic acids that are advantageously used in the preparation of the polyamine-imide are, for example, trimellitic acid, benzophenone-3,3',4'-tri-carboxylic acid and naphthalene-1,4,5-tricarboxylic acid or derivatives thereof.

In addition, a diacid or a derivative thereof, such as an acid chloride, may be used in the same reaction system to create the amide-imide bond; examples of these acids are isophthalic acid and terephthalic acid, which are optionally substituted. Other dicarboxylic acids and acid chlorides thereof are mentioned on column 3, line 32 and column 4, line 42 of the said document, to which reference may be made.

The diamines are mentioned in column 1, line 44-column 2, line 51 of the said document, to which reference may be made.

An example of a polyimide-amide prepared in the said document is obtained by reacting 100 mol of 4,4'-diisocyanatodiphenylmethane with 80 mol of trimellitic anhydride, 16 mol of terephthalic acid and 4 mol of the sodium salt of 5-sulphoisophthalic acid.

Other aromatic polyimide-amides that may be used in the compositions of the invention form the subject of document FR-A-2 079 785, which describes glossy yarns based on polyimide-amide containing at least 3% of units or sequences derived from alkali metal or alkaline-earth metal 3,5-dicarboxybenzene-sulphonate, by wet spinning of a solution of polymer in N-methylpyrrolidone, in an aqueous coagulant bath also containing N-methylpyrrolidone, followed by drawing, washing and drying.

The compositions of the invention may also comprise aromatic polyimide-amide fibres, the polymer of which is described in document EP-A1-0 360 728.

This polymer comprises:
amide-imide units of formula:

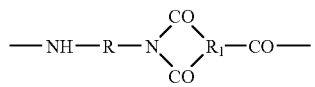
(I)

amide units of formula:

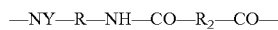

and, optionally, amide units of formula:

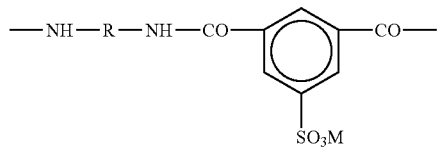

in which, and as already mentioned above, R represents a divalent aromatic radical, $R_1$ represents a trivalent aromatic radical, $R_2$ represents a divalent aromatic radical and M is an alkali metal or alkaline-earth metal.

Preferably, the units (I) represent from 80% to 100% of the units, the units (II) represent from 1% to 5% of the units and the units (III) represent from 0% to 20% of all the units.

The polyimide-amides (PIA) in the said document are obtained by polycondensation in any suitable solvent:
of at least one diisocyanate of formula:

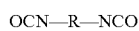

in which R is a divalent aromatic group already defined above, such as 4,4'-diisocyanato-diphenylmethane and, preferably, 4,4'-diisocyanato-diphenyl ether, or mixtures thereof, with:
an aromatic acid anhydride, such as trimellitic anhydride;
an aromatic diacid, such as terephthalic acid;
and, optionally, an alkali or alkaline-earth metal dicarboxybenzenesulphonate, preferably sodium or potassium dicarboxy-benzenesulphonate.

The yarns and fibres in the said document have a chemical structure, as defined above, in which R is a radical such as:

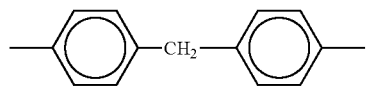

and, preferably:

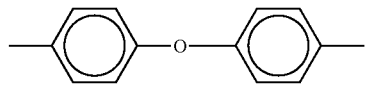

and $R_1$, preferably, a radical:

$R_2$, preferably, a radical:

and M is preferably Na or K.

The PIA yarns according to the said document are obtained by wet spinning, using solutions of polymer in a solvent or solvent mixture. The concentration of the spinning solutions is between 4% and 35% and preferably between 5% and 35%. The polymers are dissolved in a solvent or a solvent mixture containing from 5% to 100% by weight of dimethyl-ethyleneurea of pH<7 and 0 to 55% of an anhydrous aprotic polar solvent, such as N-methylpyrrolidone, dimethylacetamide, dimethylformamide, tetramethylurea or γ-butyrolactone.

The solutions that may be used must have a viscosity of between 100 and 200 poises and preferably between 150 and 160 poises. They must also contain various adjuvants, such as pigments and matting agents, to improve certain properties.

The PIA solutions are spun in a binary or ternary aqueous coagulant bath containing a solvent or a solvent mixture, in a proportion of 30% to 80% solvent and 20% to 70% water, and preferably 40% to 70% solvent(s).

The solvent used may be dimethylformamide, dimethylethyleneurea or a mixture thereof. The spinning bath is maintained at between 15 and 40° C. and preferably 20 to 30° C. The length of the coagulant bath may be adapted generally as a function of the solvent concentration and the temperature. Baths having a higher content of solvent make it possible to obtain yarns with better drawability and thus better final properties. However, when the solvent concentration is higher, a longer bath is necessary. The filaments leaving the coagulant bath in gel form are then drawn, for example in air at a ratio defined by the expression V2/V1×100, V2 being the speed of the drawing rollers, and V1 the speed of the feed rollers. The draw ratio of the yarns in gel form is at least 100% and preferably at least 110% or even higher.

After drawing, the filaments are washed using known means to free them of the solvent(s). This washing may be performed, for example, in successive vats, in which water circulates counter-currentwise or on washing rollers or by any other means, preferably at room temperature.

The washed filaments are then dried by known means, for example in a dryer or on rollers. The temperature of this drying operation may vary within a wide range, as may the speed, which is proportionately higher the higher the temperature. It is generally advantageous to perform a drying operation with gradual increase of the temperature, this temperature possibly reaching and even exceeding 200° C., for example.

The filaments may then optionally undergo hot overdrawing to improve their mechanical qualities and in particular their resilience, which may be advantageous for certain uses.

This hot overdrawing operation may be performed by any known means: oven, plate, roller, roller and plate, preferably in a closed chamber. It should be performed at a temperature of at least 150° C., which may be up to and even exceed 200 to 300° C. Its ratio is generally at least 150%, but may vary within a wide range, depending on the desired qualities for the finished yarn. The total draw ratio is at least 250% and preferably at least 260%.

The combined drawing and overdrawing operations may be performed in one or more stages, in continuous or batchwise mode, with the preceding operations. Furthermore, the secondary drawing operation may be combined with the drying operation. To do this, it suffices to provide, at the end of the drying operation, a zone of higher temperature allowing the overdrawing operation.

In order to be incorporated into the composition of the invention, the filaments are then chopped into fibres of the desired length, mentioned above.

A polymer forming the subject of this document and which can form the fibres included in the compositions of the invention is prepared from the following monomers:
trimellitic anhydride: 40 mol %;
isophthalic acid: 8 mol %;
sodium salt of 5-sulphoisophthalic acid: 2 mol %;
4,4'-diisocyanatodiphenyl ether: 50 mol %.

Document EP-A-0 549 494 also describes fibres based on polyimide-amides that may be incorporated into the compositions of the invention. These are PAI fibres consisting of:
amide-imide units of formula (I);
optionally, units of formula (II);
optionally, units of formula (III);
units of formula (IV).

$R$, $R_1$, $R_2$, $R_3$ and $R_4$ have the meaning already given above. In particular, R represents a tolylene and/or meta-phenylene radical. The units (I) are present in a proportion of from 0 to 100% and preferably from 20% to 100%, the units (II) are present in a proportion of from 0 to less than 100%, the units (III) are present in a proportion of from 0 to 5% and the units (IV) are present in a proportion of from 0 to less than 100% and preferably from 0 to 80%. The sum of the units (I), (II), (III) and (IV) is equal to 100%.

As already mentioned above, the preferred aromatic polyimide-amide fibres are Kermel Tech® fibres, in which the polyimide-amide comprises repeating units of formula:

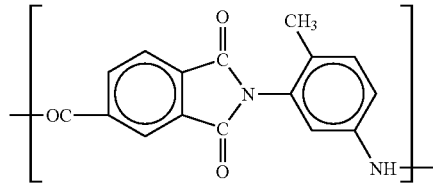

and is obtained by polycondensation of tolylene diisocyanate and trimellitic anhydride.

The composition according to the invention is makeup composition, a makeup base, a top coat composition to be applied over a makeup, or a cosmetic treatment or care composition for keratin materials or fibres.

The composition according to the invention applies more particularly to the eyelashes. Accordingly, the composition of the invention may be a composition for coating the eyelashes, especially an eyelash makeup composition, also known as a mascara, a composition to be applied over an eyelash makeup, also known as a top coat, or a composition for treating the eyelashes, especially human eyelashes or false eyelashes. The composition is more especially a mascara.

In the present patent application, the term "physiologically acceptable medium" means a non-toxic medium that is compatible with human keratin materials, especially the eyelashes or the eyebrows, for instance a cosmetic medium, the cosmetic medium possibly being a hydrophilic or lipophilic cosmetic medium.

The composition according to the invention may comprise an aqueous medium, constituting an aqueous phase, which may be the continuous phase of the composition.

The composition may comprise water and optionally one or more hydrophilic organic solvent(s), i.e. one or more water-miscible organic solvent(s), for instance alcohols and especially monoalcohols containing from 2 to 5 carbon atoms, for instance ethanol, isopropanol or n-propanol, polyols containing from 2 to 8 carbon atoms, for instance glycerol, diglycerol, propylene glycol, ethylene glycol, 1,3-butylene glycol, sorbitol, pentylene glycol, $C_3$-$C_4$ ketones and $C_2$-$C_4$ aldehydes.

The water or the mixture of water and hydrophilic organic solvent(s) may be present in the composition according to the invention in a content ranging from 0.1% to 90% by weight and preferably from 0.1% to 60% by weight relative to the total weight of the composition.

The composition may also comprise a fatty phase, which may comprise fatty substances chosen from oils, organic solvents, waxes and pasty fatty substances, and mixtures thereof. The fatty phase may form a continuous phase of the composition. In particular, the composition according to the invention may be anhydrous.

The fatty phase may consist especially of any physiologically acceptable and in particular cosmetically acceptable oil, chosen especially from carbon-based oils, hydrocarbon-based oils, fluoro oils and/or silicone oils of mineral, animal, plant or synthetic origin, alone or as a mixture.

The total fatty phase of the composition may represent from 0.1% to 98% by weight and preferably from 1% to 80% by weight relative to the total weight of the composition.

Advantageously, the fatty phase of the composition may comprise at least one volatile organic solvent or oil and/or at least one non-volatile oil. More preferably, the fatty phase comprises at least one volatile oil.

For the purposes of the invention, the expression "volatile compound", for example "volatile oil or organic solvent", means any compound (or non-aqueous medium) that can evaporate on contact with the skin or the keratin fibre or material in less than one hour at room temperature and atmospheric pressure. The volatile compound, for example the volatile organic solvent(s) and the volatile oils of the invention, is a volatile cosmetic compound (these are, for example, organic solvents and volatile cosmetic oils), which is liquid at room temperature, especially having a nonzero vapour pressure at room temperature and atmospheric pressure, ranging in particular from $10^{-3}$ to 300 mmHg (0.13 Pa to 40 000 Pa), more particularly ranging from 1.3 Pa to 13 000 Pa (0.01 to 100 mmHg) and even more particularly ranging from 1.3 Pa to 1 300 Pa (0.01 to 10 mmHg). In contrast, the term "non-volatile compound", for example "non-volatile oil", means a compound for example an oil that remains on the skin or the keratin fibre or material at room temperature and atmospheric pressure for at least several hours and that especially has a vapour pressure of less than $10^3$ mmHg (0.13 Pa).

These oils may be hydrocarbon-based oils, silicone oils or fluorinated oils, or mixtures thereof.

The term "hydrocarbon-based oil" means an oil mainly containing hydrogen and carbon atoms and optionally oxygen, nitrogen, sulphur or phosphorus atoms. The volatile hydrocarbon-based oils may be chosen from hydrocarbon-based oils containing from 8 to 16 carbon atoms, and especially branched $C_8$-$C_{16}$ alkanes, for instance $C_8$-$C_6$ isoalkanes of petroleum origin (also known as isoparaffins), for instance isododecane (also known as 2,2,4,4,6-pentamethylheptane), isodecane and isohexadecane, for example the oils sold under the trade names Isopar or Permetyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used. The volatile solvent is preferably chosen from volatile hydrocarbon-based oils containing from 8 to 16 carbon atoms, and mixtures thereof.

Volatile oils that may also be used include volatile silicones, for instance volatile linear or cyclic silicone oils, especially those with a viscosity $\leq 6$ centistokes ($6 \times 10^{-6}$ m$^2$/s) and especially containing from 2 to 10 silicon atoms, these silicones optionally comprising alkyl or alkoxy groups containing from 1 to 22 carbon atoms. As volatile silicone oils that may be used in the invention, mention may be made especially of octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane and dodecamethyl pentasiloxane, and mixtures thereof.

Volatile fluorinated solvents such as nonafluoromethoxybutane or perfluoromethylcyclopentane may also be used.

The volatile oil may be present in the composition according to the invention in a content ranging from 0.1% to 98% by weight and preferably from 1% to 65% by weight relative to the total weight of the composition.

The composition may also comprise at least one non-volatile oil chosen especially from non-volatile hydrocarbon-based oils and/or silicone and/or fluorinated oils.

Non-volatile hydrocarbon-based oils that may especially be mentioned include:

hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially wheatgerm oil, sunflower oil, grapeseed oil, sesame seed oil, maize oil, apricot oil, castor oil, karite oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel, synthetic ethers containing from 10 to 40 carbon atoms;

linear or branched hydrocarbons of mineral or synthetic origin, such as petroleum jelly, polydecenes, hydrogenated polyisobutene such as parleam, and squalane, and mixtures thereof;

synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_5+R_6 \geq 10$, such as, for example, purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid;

and mixtures thereof.

The non-volatile silicone oils that may be used in the composition according to the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenylsilicones, for instance phenyltrimethicones, phenyldimethicones, phenyltrimethylsiloxydiphenylsiloxanes, diphenyldimethicones, diphenylmethyldiphenyltrisiloxanes and 2-phenylethyl-trimethylsiloxysilicates.

The fluorinated oils that may be used in the invention are, in particular, fluorosilicone oils, fluorinated polyethers or fluorinated silicones, as described in document EP-A-847 752.

The non-volatile oils may be present in the composition according to the invention in a content ranging from 0.1% to 80% by weight, preferably from 0.1% to 50% by weight and better still from 0.1% to 20% by weight, relative to the total weight of the composition.

The fatty phase of the composition according to the invention may comprise a wax. For the purposes of the present invention, the term "wax" means a lipophilic fatty compound that is solid at room temperature (25° C.) and atmospheric pressure (760 mmHg, i.e. $10^5$ Pa), with a reversible solid/liquid change of state, having a melting point of greater than 30° C. and better still greater than 55° C., which may be up to 200° C. and especially up to 120° C.

By bringing the wax to its melting point, it is possible to make it miscible with oils and to form a microscopically homogeneous mixture, but on cooling the mixture to room temperature, recrystallization of the wax in the oils of the mixture is obtained.

The melting point values correspond, according to the invention, to the melting peak measured using a differential scanning calorimeter (D.S.C.), for example the calorimeter sold under the name DSC 30 by the company Mettler, with a temperature rise of 5 or 10° C. per minute.

For the purposes of the invention, the waxes are those generally used in cosmetics and dermatology. Mention may be made especially of beeswax, lanolin wax and Chinese insect waxes; rice wax, carnauba wax, candelilla wax, ouricury wax, cork fibre wax, sugar cane wax, Japan wax and sumach wax; montan wax, microcrystalline waxes, paraffin waxes, ozokerites, ceresin wax, lignite wax, polyethylene waxes, the waxes obtained by Fischer-Tropsch synthesis, and fatty acid esters of glycerides that are solids at 40° C. and better still at more than 55° C.

Mention may also be made of the waxes obtained by catalytic hydrogenation of animal or plant oils containing linear or branched $C_8$-$C_{32}$ fatty chains. Among these, mention may be made especially of hydrogenated jojoba oil, hydrogenated sunflower oil, hydrogenated castor oil, hydrogenated coconut oil and hydrogenated lanolin oil.

Mention may also be made of silicone waxes or fluorinated waxes.

The waxes present in the composition may be dispersed in the form of particles in an aqueous medium. These particles may have a mean size ranging from 50 nm to 10 µm and preferably from 50 nm to 3.5 µm.

In particular, the wax may be present in the form of a wax-in-water emulsion, the waxes possibly being in the form of particles with a mean size ranging from 1 µm to 10 µm and preferably from 1 µm to 3.5 µm.

In another embodiment of the composition according to the invention, the wax may be present in the form of a wax microdispersion, the wax being in the form of particles with a mean size of less than 1 µm and ranging especially from 50 nm to 500 nm. Wax microdispersions are described in documents EP-A-557 196 and EP-A-1 048 282.

The wax may also have a hardness ranging from 0.05 MPa to 15 MPa and preferably ranging from 6 MPa to 15 MPa. The hardness is determined by measuring the compressive strength, measured at 20° C. using a texturometer sold under the name TA-XT2i by the company Rheo, equipped with a stainless-steel cylinder 2 mm in diameter travelling at a measuring speed of 0.1 mm/s, and penetrating into the wax to a penetration depth of 0.3 mm. To measure the hardness, the wax is melted at a temperature equal to the melting point of the wax +20° C. The molten wax is cast in a container 30 mm in diameter and 20 mm deep. The wax is recrystallized at room temperature (25° C.) over 24 hours and is then stored for at least 1 hour at 20° C. before performing the hardness measurement. The value of the hardness is the compressive strength measured divided by the area of the texturometer cylinder in contact with the wax.

The wax may be present in the composition according to the invention in a content ranging from 0.1% to 50% by weight, preferably from 0.5% to 30% by weight and better still from 1% to 20% by weight, relative to the total weight of the composition.

The composition according to the invention may contain at least one fatty compound that is pasty at room temperature. For the purposes of the invention, the expression "pasty fatty substance" means fatty substances with a melting point ranging from 20 to 55° C., preferably 25 to 45° C., and/or a viscosity at 40° C. ranging from 0.1 to 40 Pa.s (1 to 400 poises), preferably 0.5 to 25 Pa.s, measured using a Contraves TV or Rheomat 80 viscometer, equipped with a spindle rotating at 60 Hz. A person skilled in the art can select the spindle for measuring the viscosity from the spindles MS-r3 and MS-r4, on the basis of his general knowledge, so as to be able to carry out the measurement of the pasty compound tested.

These fatty substances are preferably hydrocarbon-based compounds, optionally of polymeric type; they can also be chosen from silicone and/or fluorinated compounds; they may also be in the form of a mixture of hydrocarbon-based and/or silicone and/or fluorinated compounds. In the case of a mixture of different pasty fatty substances, the hydrocarbon-based pasty compounds (containing mainly hydrogen and carbon atoms and optionally ester groups) are preferably used in major proportion.

Among the pasty compounds which may be used in the composition according to the invention, mention may be made of lanolins and lanolin derivatives such as acetylated lanolins or oxypropylenated lanolins or isopropyl lanolate, having a viscosity of from 18 to 21 Pa.s, preferably 19 to 20.5 Pa.s, and/or a melting point of from 30 to 55° C., and mixtures thereof. It is also possible to use esters of fatty acids or of fatty alcohols, in particular those containing from 20 to 65 carbon atoms (melting point of about from 20 to 35° C. and/or viscosity at 40° C. ranging from 0.1 to 40 Pa.s), such as triisostearyl or cetyl citrate; arachidyl propionate; polyvinyl laurate; cholesterol esters, such as triglycerides of plant origin, such as hydrogenated plant oils, viscous polyesters such as poly (12-hydroxystearic acid), and mixtures thereof. Triglycerides of plant origin that may be used include hydrogenated castor oil derivatives, such as "Thixinr" from Rhéox.

Mention may also be made of pasty silicone fatty substances such as polydimethylsiloxanes (PDMSs) containing pendent chains of the alkyl or alkoxy type containing from 8 to 24 carbon atoms, and having a melting point of 20-55° C., such as stearyldimethicones, in particular those sold by Dow Corning under the trade names DC2503 and DC25514, and mixtures thereof.

The pasty fatty substance may be present in the composition according to the invention in a proportion of from 0% to 60% (especially 0.01% to 60%) by weight, relative to the total weight of the composition, preferably in a proportion of from 0.5% to 45% by weight, and better still ranging from 2% to 30% by weight, in the composition.

The composition according to the invention can contain emulsifying surfactants, present in particular in a proportion ranging from 2% to 30% by weight relative to the total weight of the composition, and better still from 5% to 15%. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of the said reference, for the anionic and nonionic surfactants.

The surfactants preferably used in the composition according to the invention are chosen from:
  nonionic surfactants: fatty acids, fatty alcohols, polyethoxylated or polyglycerolated fatty alcohols such as polyethoxylated stearyl or cetylstearyl alcohols, fatty acid esters of sucrose, alkyl glucose esters, in particular polyoxyethylenated fatty esters of $C_1$-$C_6$ alkyl glucose, and mixtures thereof;
  anionic surfactants: $C_{16}$-$C_{30}$ fatty acids neutralized with amines, aqueous ammonia or alkaline salts, and mixtures thereof.

Surfactants which make it possible to obtain an oil-in-water or wax-in-water emulsion are preferably used.

The composition according to the invention may comprise a film-forming polymer.

The film-forming polymer may be a polymer that is dissolved or dispersed in the form of particles in an aqueous phase of the composition, or dissolved or dispersed in the form of particles in a liquid fatty phase. The composition may comprise a blend of these polymers.

The film-forming polymer may be. present in the composition according to the invention in a solids content ranging from 0.1% to 60% by weight, preferably from 0.5% to 40% by weight and better still from 1% to 30% by weight, relative to the total weight of the composition.

In the present application, the expression "film-forming polymer" means a polymer which is capable, by itself or in the presence of an auxiliary film-forming agent, of forming a continuous and adherent film on a support, in particular on keratin materials.

A film-forming polymer capable of forming a hydrophobic film, i.e. a polymer whose film has a solubility in water at 25° C. of less than 1% by weight, is preferably used.

Among the film-forming polymers which may be used in the composition of the present invention, mention may be made of synthetic polymers, of radical-mediated type or of polycondensate type, and polymers of natural origin, and mixtures thereof.

The expression "radical-mediated film-forming polymer" means a polymer obtained by polymerization of monomers containing unsaturation, in particular ethylenic unsaturation, each monomer being capable of homopolymerizing (unlike polycondensates).

The film-forming polymers of radical-mediated type may be, in particular, vinyl polymers or copolymers, in particular acrylic polymers.

The vinyl film-forming polymers can result from the polymerization of monomers containing ethylenic unsaturation and containing at least one acidic group and/or esters of these acidic monomers and/or amides of these acidic monomers.

Monomers bearing an acidic group which may be used are $\alpha,\beta$-ethylenic unsaturated. carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates which may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates which may be mentioned are hydroxyethyl acrylate, 2-hydroxypropyl acrylate, hydroxyethyl methacrylate and 2-hydroxypropyl methacrylate.

Among the aryl (meth)acrylates which may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted with fluorine atoms.

Examples of amides of the acid monomers that may be mentioned are (meth)acrylamides, and especially N-alkyl (meth)acrylamides, in particular of a $C_2$-$C_{12}$ alkyl. Among the N-alkyl(meth)acrylamides which may be mentioned are N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and $\alpha$-methylstyrene.

It is possible to use any monomer known to the man skilled in the art that falls with the categories of acrylic monomers and vinyl monomers (including monomers modified by a silicone chain).

Among the film-forming polycondensates that may be mentioned are polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinyl-pyrrolidones, polyester-polyurethanes, polyether-polyurethanes, polyureas and polyurea/polyurethanes, and mixtures thereof.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, the ones preferentially chosen are phthalic acid, isophthalic acid and terephthalic acid.

The diol may be chosen from aliphatic, alicyclic and aromatic diols. The diol used is preferably chosen from: ethylene glycol, diethylene glycol, triethylene glycol, 1,3-propanediol, cyclohexanedimethanol and 4-butanediol.

Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines which may be used are ethylenediamine, hexamethylenediamine and meta- or para-phenylenediamine. An amino alcohol which may be used is monoethanolamine.

The polyester may also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular.

The aromatic nucleus of the difunctional aromatic monomer also bearing a group —$SO_3M$ as described above may be chosen, for example, from benzene, naphthalene, anthracene, biphenyl, oxybiphenyl, sulphonylbiphenyl and methylenebiphenyl nuclei. As examples of difunctional aromatic monomers also bearing a group —$SO_3M$, mention may be made of: sulphoisophthalic acid, sulphoterephthalic acid, sulphophthalic acid, 4-sulphonaphthalene-2,7-dicarboxylic acid.

The copolymers preferably used are those based on isophthalate/sulphoisophthalate, and more particularly copolymers obtained by condensation of diethylene glycol, cyclohexanedimethanol, isophthalic acid and sulphoisophthalic acid. Such polymers are sold, for example, under the brand name Eastman AQ® by the company Eastman Chemical Products.

The optionally modified polymers of natural origin may be chosen from shellac resin, sandarac gum, dammar resins, elemi gums, copal resins and cellulose-based polymers, and mixtures thereof.

According to a first embodiment of the composition according to the invention, the film-forming polymer may be present in the form of particles in aqueous dispersion, generally known as a latex or pseudolatex. The techniques for preparing these dispersions are well known to the man skilled in the art.

Aqueous dispersions of film-forming polymers which may be used are the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer.

Aqueous dispersions of film-forming polymer that may also be used include polymer dispersions resulting from the free-radical polymerization of one or more radical monomers within and/or partially at the surface of pre-existing particles of at least one polymer chosen from the group consisting of polyurethanes, polyureas, polyesters, polyesteramides and/or alkyds. These polymers are generally known as hybrid polymers.

According to a second working variant of the composition according to the invention, the film-forming polymer may be a water-soluble polymer and is thus present in the aqueous phase of the composition in dissolved form. Examples of water-soluble film-forming polymers that may be mentioned include:

- proteins, for instance proteins of plant origin such as wheat proteins and soybean proteins; proteins of animal origin such as keratins, for example keratin hydrolysates and sulphonic keratins;
- anionic, cationic, amphoteric or nonionic chitin or chitosan polymers;
- polymers of celluloses such as hydroxyethylcellulose, hydroxypropylcellulose, methylcellulose, ethylhydroxyethylcellulose and carboxymethylcellulose, and quaternized cellulose derivatives;
- acrylic polymers or copolymers, such as polyacrylates or polymethacrylates;
- vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;
- polymers of natural origin, which are optionally modified, such as:
- gum arabics, guar gum, xanthan derivatives, karaya gum; alginates and carrageenans;
- glycoaminoglycans, hyaluronic acid and derivatives thereof;
- shellac resin, sandarac gum, dammar resins, elemi gums and copal resins;
- deoxyribonucleic acid;
- mucopolysaccharides such as hyaluronic acid and chondroitin sulphate, and mixtures thereof.

According to another working variant of the composition according to the invention, the film-forming polymer may be present in a liquid fatty phase comprising organic solvents or oils such as those described above. For the purposes of the invention, the expression "liquid fatty phase" means a fatty phase which is liquid at room temperature (25° C.) and atmospheric pressure (760 mmHg, i.e. $10^5$ Pa), composed of one or more fatty substances that are liquid at room temperature, also known as oils, which are generally mutually compatible.

The liquid fatty phase preferably comprises a volatile oil, optionally mixed with a non-volatile oil, the oils possibly being chosen from those mentioned above.

According to a third embodiment of the composition according to the invention, the film-forming polymer may be present in the form of surface-stabilized particles dispersed in the liquid fatty phase.

The dispersion of surface-stabilized polymer. particles may be manufactured as described in document EP-A-749 747.

The polymer particles are surface-stabilized by means of a stabilizer that may be a block polymer, a grafted polymer and/or a random polymer, alone or as a blend.

Dispersions of film-forming polymer in the liquid fatty phase, in the presence of stabilizers, are described especially in documents EP-A-749 746, EP-A-923 928 and EP-A-930 060, the content of which is incorporated into the present patent application by reference.

The size of the polymer particles in dispersion either in the aqueous phase or in the liquid fatty phase may range from 5 nm to 600 nm and preferably 20 nm to 300 nm.

According to a fourth embodiment of the composition according to the invention, the film-forming polymer may be dissolved in the liquid fatty phase, in which case the film-forming polymer is said to be a liposoluble polymer.

Examples of liposoluble polymers which may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, the aim of which is to [lacuna] which may be either of the vinyl type or of the allylic or methallylic type, such as tetraallyloxyethane, divinylbenzene, divinyl octanedioate, divinyl dodecanedioate and divinyl octadecanedioate.

Examples of these copolymers which may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of liposoluble film-forming polymers which may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble homopolymers may be chosen from polyvinyl stearate copolymers, polyvinyl stearate copolymers crosslinked with divinylbenzene, with diallyl ether or with diallyl phthalate, polystearyl (meth)acrylate copolymers, polyvinyl laurate copolymers and polylauryl (meth)acrylate copolymers, it being possible for these poly(meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2 000 to 500 000 and preferably from 4 000 to 200 000.

As liposoluble film-forming polymers which may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The composition according to the invention may comprise an auxiliary film-forming agent that promotes the formation of a film with the film-forming polymer. Such a film-forming agent may be chosen from any compound known to those skilled in the art as being capable of satisfying the desired function, and may be chosen especially from plasticizers and coalescers.

The composition according to the invention may also comprise a dyestuff, for instance pulverulent dyestuffs, liposoluble dyes and water-soluble dyes. This dyestuff may be present in a content ranging from 0.01% to 30% by weight relative to the total weight of the composition.

The pulverulent dyestuffs may be chosen from pigments and nacres.

The pigments may be white or coloured, mineral and/or organic, and coated or uncoated. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D & C type, and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, in particular, ferric blue or chromium oxide, titanium mica with an organic pigment of the abovementioned type, and nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

The composition according to the invention may also comprise fillers. The term "fillers" should be understood as meaning colourless or white, mineral or synthetic particles of any shape, which are insoluble in the medium of the composition irrespective of the temperature at which the composition is manufactured. These fillers serve especially to modify the rheology or the texture of the composition.

The fillers may be mineral or organic and of any shape, in platelet form, spherical or oblong, irrespective of the crystallographic shape (for example leaflet, cubic, hexagonal, orthorhombic, etc.). Mention may be made of talc, mica, silica, kaolin, powders of polyamide, for instance Nylon® (Orgasol® from Atochem), of poly-β-alanine and of polyethylene, powders of tetrafluoroethylene polymers, for instance Teflon®, lauroyllysine, starch, boron nitride, hollow polymer microspheres such as those of polyvinylidene chloride/acrylonitrile, for instance Expancel® (Nobel Industrie), acrylic acid copolymers such as Polytrap® (Dow Corning) and silicone resin microbeads (for example Tospearls® from Toshiba), polyorganosiloxane elastomer particles, precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

The fillers may be present in a proportion of from 0.01% to 30% by weight and preferably 0.5% to 15% by weight.

The composition of the invention. may. also comprise any additive usually used in cosmetics, such as antioxidants, fillers, preserving agents, fragrances, neutralizers, thickeners, surfactants, cosmetic or dermatological active agents, for instance emollients, moisturizers, vitamins, sunscreens, plasticizers and coalescers, and mixtures thereof. These additives may be present in the composition in a content ranging from 0.01% to 20% and better still ranging from 0.01% to 10% of the total weight of the composition.

Needless to say, a person skilled in the art will take care to select the optional additional additives and/or the amount thereof such that the advantageous properties of the composition according to the invention are not, or are not substantially, adversely affected by the envisaged addition.

The composition according to the invention may be manufactured by the known processes generally used in cosmetics or dermatology.

The invention also relates to a cosmetic treatment or makeup process for keratin materials, comprising the application to the said keratin materials of the composition as described above.

The invention also relates to a process for coating the eyelashes, comprising the application to the eyelashes of the composition described above.

The invention also relates to the use of the composition as described above to obtain a lengthening of the eyelashes that is exactly in line with them, or to give the eyelashes an even (uniform) lengthening effect.

The invention also relates to the use, in a mascara, of fibres as defined above to obtain a lengthening of the eyelashes that is exactly in line with them or to give the eyelashes an even lengthening effect.

Finally, the invention relates to the use, in a mascara, of fibres as defined above, to mimic or imitate natural eyelashes, and also to the use of a composition as described above, such as a mascara, to mimic or imitate natural eyelashes.

The invention is illustrated in greater detail in the examples that follow.

EXAMPLE 1

A mascara having the composition below was prepared:

| | |
|---|---|
| Polyimide-amide fibres 2 mm long sold under the name Kermel Tech by the company Rhodia | 1 g |
| Saponite (Veegum DGT from the company Vanderbilt) | 10 g |
| Black iron oxide | 7 g |
| Propylene glycol | 7 g |
| Preservatives | qs |
| Water qs | 100 g |

The mascara is easy to apply to the eyelashes and gives them an even (uniform) lengthening effect: the rigid fibres are fixed in line with the eyelashes.

EXAMPLE 2

A mascara having the composition below was prepared:

| | |
|---|---|
| Polyimide fibres 3 mm long chopped using the fibre sold under the name Fibre Nomex Brand 430 by the company Dupont de Nemours | 1 g |
| Saponite (Veegum DGT from the company Vanderbilt) | 10 g |
| Black iron oxide | 7 g |
| Propylene glycol | 7 g |
| Preservatives | qs |
| Water qs | 100 g |

The mascara is easy to apply to the eyelashes and gives them an even (uniform) lengthening effect: the rigid fibres are fixed in line with the eyelashes.

The above written description of the invention provides a manner and process of making and using it such that any person skilled in this art is enabled to make and use the same, this enablement being provided in particular for the subject matter of the appended original claims, which make up a part of the invention description, and including a cosmetic composition comprising rigid, substantially rectilinear fibers of a synthetic polymer in a physiologically acceptable medium, in which the polymer is chosen from polyurethanes, polyesters, acrylic polymers, polyolefins, non-aromatic polyamides and aromatic polyimide-amides.

All references, patents, applications, tests, standards, documents, publications, brochures, texts, articles, etc. mentioned herein are incorporated herein by reference. Where a numerical limit or range is stated, all values and subranges therewithin are specifically included as if explicitly written out.

The invention claimed is:

1. A mascara composition comprising rigid, substantially rectilinear polymeric fibers in a physiologically acceptable medium, wherein the polymer is selected from the group consisting of non-aromatic polyamides, aromatic polyimide-amides comprising a repeating unit of formula (I):

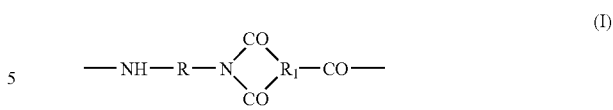

optionally, also, a repeating unit of formula (II):

$$-NH-R-NH-CO-R_2-CO- \quad (II)$$

optionally, also, a repeating unit of formula (III):

(III)

$$-NH-R-NH-CO-\underset{SO_3M}{\text{(benzene ring)}}-CO-$$

optionally, also, a repeating unit of formula (IV):

(IV)

in which R represents a divalent aromatic group, $R_2$, represents a divalent aromatic group, $R_3$ represents a tetravalent aromatic group, $R_1$ represents a trivalent aromatic group and M represents an alkali metal or alkaline-earth metal, and mixtures thereof, and wherein at least 50%, in numerical terms, of the fibers are such that the angle formed between the tangent to the central longitudinal axis of the fiber at one of the ends of the fiber and the straight line connecting said end to the point on the central longitudinal axis of the fiber corresponding to half the length of the fiber, is less than or equal to 15°, and the angle fanned between the tangent to the central longitudinal axis of the fiber at a point halfway along the fiber and the straight line connecting one of the ends to the point on the central longitudinal axis of the fiber corresponding to half the length of the fiber, is less than or equal to 15°, for the same length of fiber ranging from 0.8 mm to 5 mm.

2. The mascara composition according to claim 1, in which the angles are less than or equal to 10°.

3. The mascara composition according to claim 1, in which the fibers are from 1 to 3 mm long.

4. The mascara composition according to claim 1, in which the cross section of the fibers is within a circle of diameter (D) ranging from 2 nm to 500 um.

5. The mascara composition according to claim 1, in which the fibers have a length L and a diameter D of the circle in which the cross section of the fiber is inscribed, such that the ratio L/D is in the range from 3.5 to 2,500.

6. The mascara composition according to claim 1, in which the fibers have a yarn count in the range from 0.15 denier to 30 denier.

7. The mascara composition according to claim 1, in which the fibers are present in a content of from 0.01% to 10% by weight relative to the total weight of the composition.

8. The mascara composition according to claim 1, in which R₁ represents:

a group

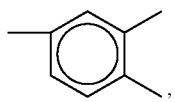

a group

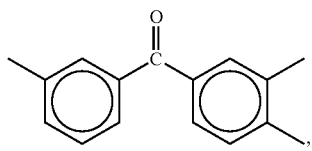

or a group

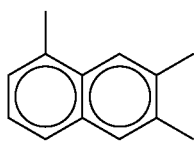

9. The mascara composition according to claim 1, in which R is chosen from groups:

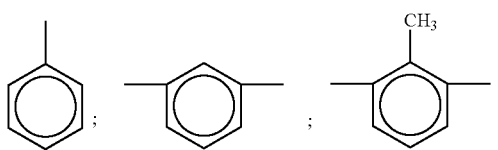

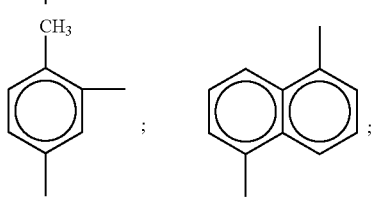

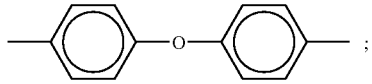

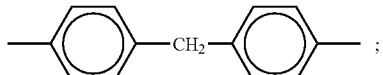

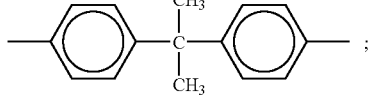

-continued

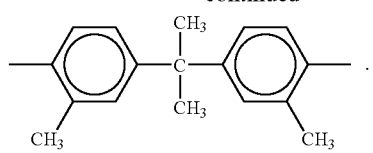

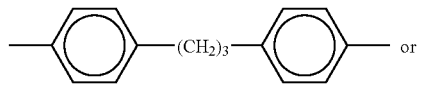

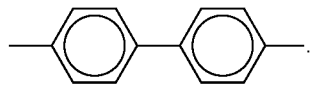

10. The mascara composition according to claim 1, in which R2 is a group of formula:

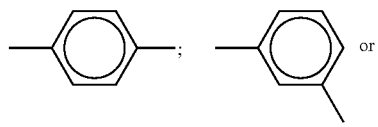

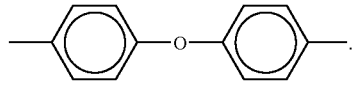

11. The mascara composition according to claim 1, in which R₃ is selected from the group consisting of:

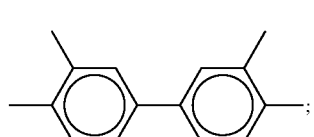

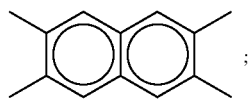

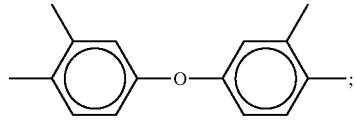

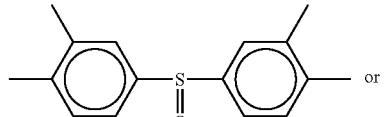

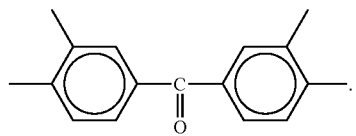

12. The mascara composition according to claim 1, in which the polyimide-amide is obtained by polymerization of tolylene diisooyanate and of trimellitic anhydride, and comprises repeating units of formula:

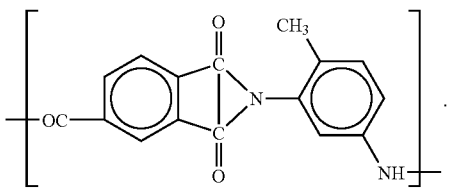

13. The mascara composition according to claim 1, in which the fibers are surface-treated and/or coated.

14. The mascara composition according to claim 1, in which an active agent and/or pigment and/or dye is incorporated into the bulk of the polymer forming the fibers.

15. The mascara composition according to claim 1, in which the physiologically acceptable medium is a hydrophilic or lipophilic cosmetic medium.

16. The mascara composition according to claim 1, further comprising water or a mixture of water and of hydrophilic organic solvent(s).

17. The mascara composition according to claim 16, comprising a hydrophilic organic solvent(s) selected from the group consisting of monoalcohols containing from 2 to 5 carbon atoms, polyols containing from 2 to 8 carbon atoms, $C_3$-$C_4$ ketones, $C_2$-$C_4$ aldehydes, and mixtures thereof.

18. The mascara composition according to claim 16, in which the water or the mixture of water and of hydrophilic organic solvent(s) is present in a content ranging from 0.1% to 90% by weight relative to the total weight of the composition.

19. The mascara composition according to claim 1, which further comprises a fatty phase.

20. The mascara composition according to claim 1, which is an anhydrous composition.

21. The mascara composition according to claim 19, in which the fatty phase comprises a fatty substance selected from the group consisting of oils, organic solvents, waxes and pasty fatty substances, and mixtures thereof.

22. The mascara composition according to claim 19, in which the fatty phase comprises at least one volatile oil.

23. The mascara composition according to claim 22, in which the volatile oil is a hydrocarbon-based oil comprising from 8 to 16 carbon atoms.

24. The mascara composition according to claim 22, in which the volatile oil is present in a content ranging from 0.1% to 98% by weight relative to the total weight of the composition.

25. The mascara composition according to claim 1, further comprising a film-forming polymer.

26. The mascara composition according to claim 25, in which the film-forming polymer is selected from the group consisting of vinyl polymers, polyurethanes, polyesters, polyamildes, polyureas, cellulose-based polymers, and mixtures thereof.

27. The mascara composition according to claim 25, in which the film-forming polymer is present in a polymer solids content ranging from 0.1% to 60% by weight relative to the total weight of the composition.

28. The mascara composition according to claim 1, further comprising a dyestuff.

29. The mascara composition according to claim 28, in which the dyestuff is selected from the group consisting of pigments, nacres, liposoluble dyes, water-soluble dyes, and mixtures thereof.

30. The mascara composition according to claim 28, in which the dyestuff is present in a content ranging from 0.01% to 30% by weight, relative to the total weight of the composition.

31. The mascara composition according to claim 1, further comprising a cosmetic additive selected from the group consisting of antioxidants, fillers, preserving agents, fragrances, neutralizers, thickeners, surfactants, cosmetic active agents, dermatological active agents, plasticizers, coalescers, and mixtures thereof.

32. A method of lengthening an eyelash, comprising applying the mascara composition of claim 1, to the eyelash in an amount sufficient to lengthen the eyelash.

33. The method of claim 32, wherein said method provides a lengthening of the eyelashes that is exactly in line with them or to give the eyelashes an even lengthening effect.

* * * * *

UNITED STATES PATENT AND TRADEMARK OFFICE
CERTIFICATE OF CORRECTION

| | | |
|---|---|---|
| PATENT NO. | : 7,754,196 B2 | Page 1 of 1 |
| APPLICATION NO. | : 10/664894 | |
| DATED | : July 13, 2010 | |
| INVENTOR(S) | : Nathalie Jager-Lezer | |

It is certified that error appears in the above-identified patent and that said Letters Patent is hereby corrected as shown below:

On the title page, and column 1, line 2:

Title, "Fiber", should read -- Fibers --

Abstract, line 9, "fibres" should read -- fibers --

Claim 1, column 32, line 43, "fanned" should read -- formed --

Claim 12, column 34, line 66, "diisooyanate" should read -- diisocyanate --

Claim 26, column 36, line 13, "polyamildes" should read -- polyamides --

Signed and Sealed this
Seventeenth Day of May, 2011

David J. Kappos
*Director of the United States Patent and Trademark Office*